United States Patent [19]
Prather et al.

[11] Patent Number: 5,247,942
[45] Date of Patent: Sep. 28, 1993

[54] GUIDE WIRE WITH SWIVEL

[75] Inventors: Richard R. Prather, Richfield; Thomas R. Hektner, Minnetonka, both of Minn.

[73] Assignee: Scimed Life Systems, Inc., Maple Grove, Minn.

[21] Appl. No.: 864,443

[22] Filed: Apr. 6, 1992

[51] Int. Cl.$^5$ ............................................. A61B 5/00
[52] U.S. Cl. ..................................... 128/772; 128/657; 604/164; 604/283
[58] Field of Search ............... 403/76, 56, 220, 221, 403/90, 122, 127; 604/164, 283; 128/772, 657, 658

[56] References Cited

U.S. PATENT DOCUMENTS

| | | | |
|---|---|---|---|
| 3,674,014 | 7/1972 | Tillander | 128/657 |
| 4,771,500 | 9/1988 | Kovacs | 403/76 |
| 4,827,941 | 5/1989 | Taylor et al. | 128/657 |
| 4,846,193 | 7/1989 | Tremulis et al. | 128/772 |
| 4,875,489 | 10/1989 | Messner et al. | 128/772 |
| 4,917,103 | 4/1990 | Gambale et al. | 128/772 |
| 4,966,163 | 10/1990 | Kraus et al. | 128/772 |
| 4,992,923 | 5/1990 | Gambale et al. | 128/772 |
| 5,031,636 | 7/1991 | Gambale et al. | 128/772 |
| 5,037,391 | 8/1991 | Hammerslag et al. | 128/772 |
| 5,109,867 | 5/1992 | Twyfold, Jr. | 128/772 |
| 5,113,872 | 5/1992 | Jahrmarkt et al. | 128/772 |
| 5,117,838 | 6/1992 | Palmer et al. | 128/657 |

FOREIGN PATENT DOCUMENTS

0347035A2 12/1989 European Pat. Off. .

OTHER PUBLICATIONS

"Guide Wire Extension," Constantin Cope, M.D., *Radiology* (1985); 157-263, p. 263.
"An Extra-Long Guide Wire For Use During Cardiac Catherization," Robert J. Adolph, M.D. and Ralph Shabetai, M.D., *Angiology* (1966), 17:119-120, pp. 119-120.

Primary Examiner—Stephen C. Pellegrino
Assistant Examiner—Gary Jackson
Attorney, Agent, or Firm—Willian Brinks Olds Hofer Gilson & Lione

[57] ABSTRACT

A guide wire, and methods of use thereof, comprising a main part, an extension part, and a connector. The connector connects the main part to the extension part such that the main part and the extension part can be rotated relative to each other.

19 Claims, 4 Drawing Sheets

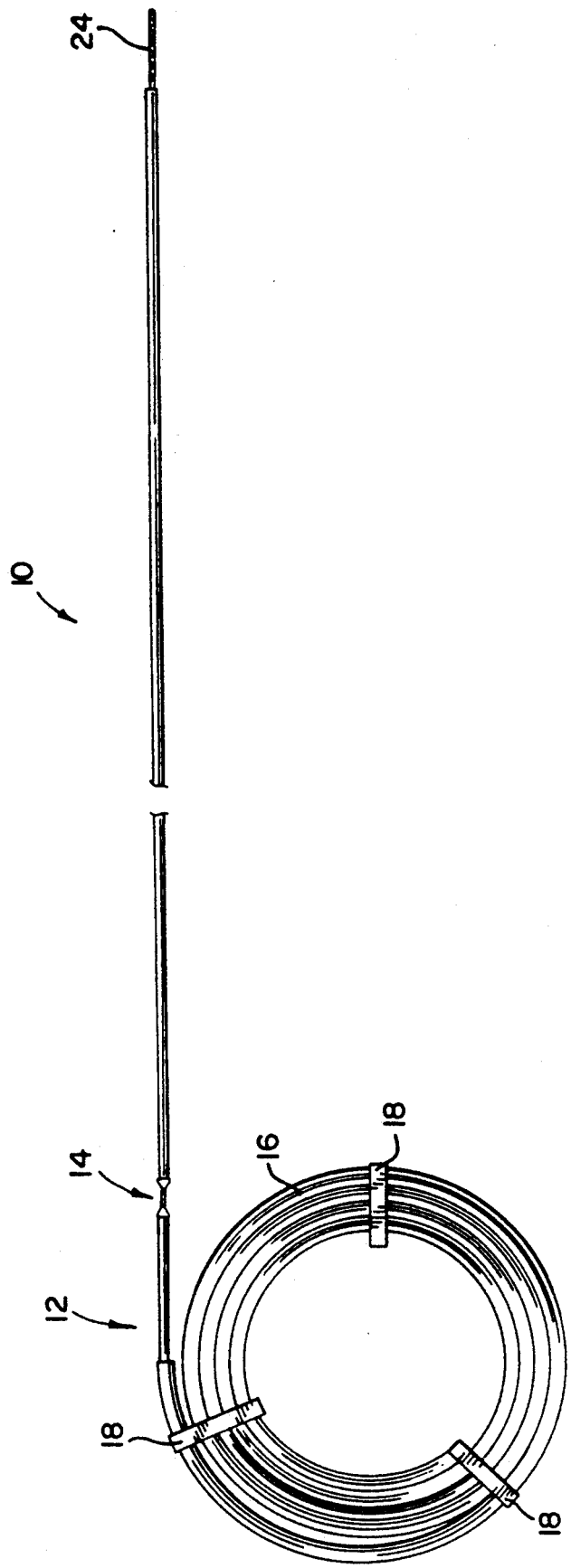

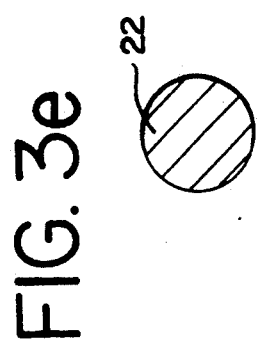
FIG.3e
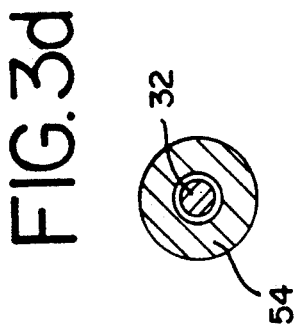
FIG.3d
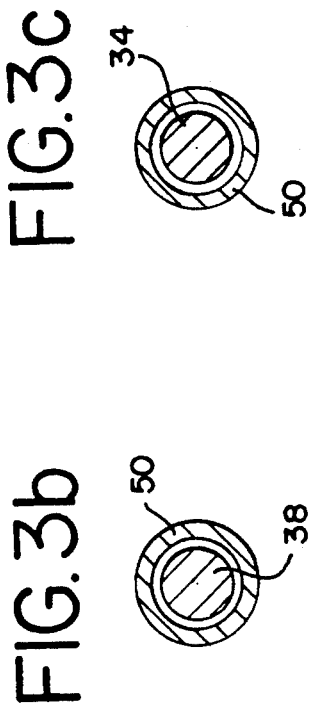
FIG.3c
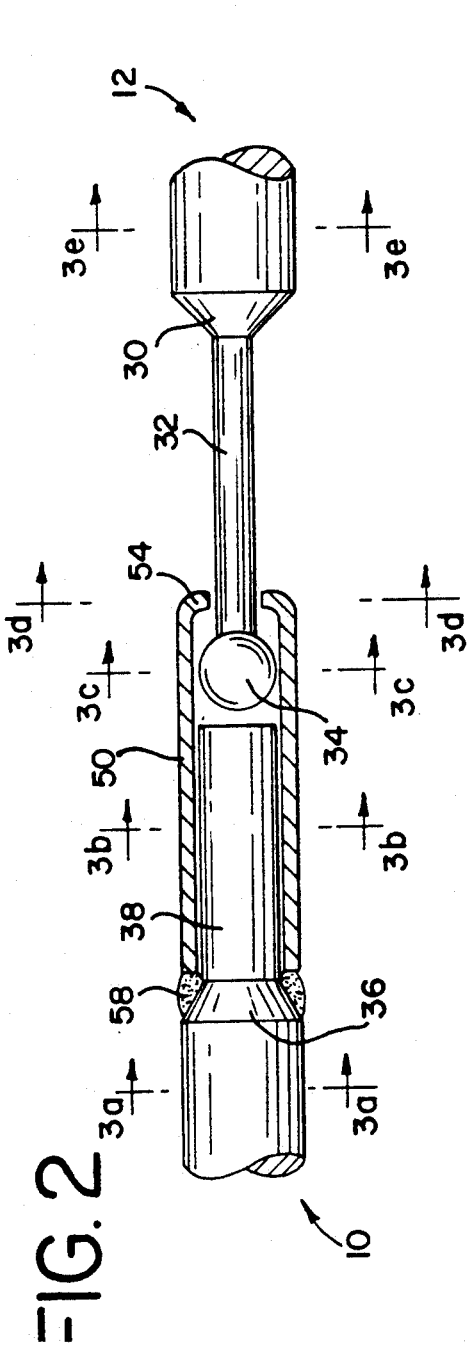
FIG.2
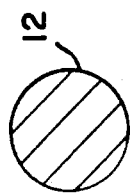
FIG.3b
FIG.3a

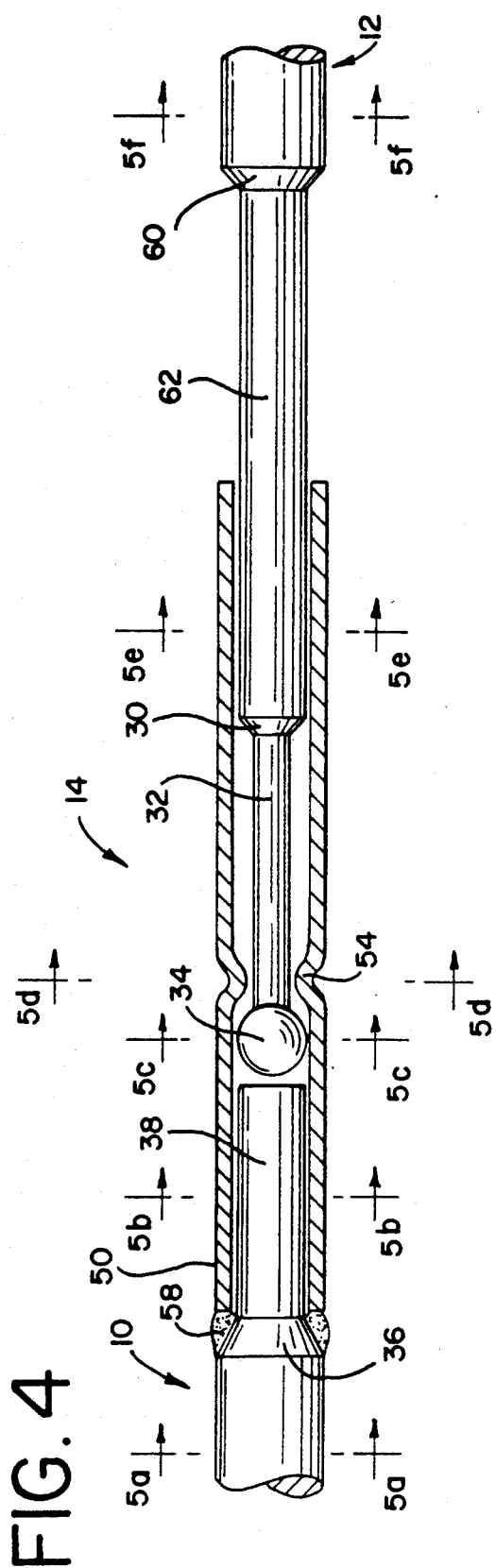
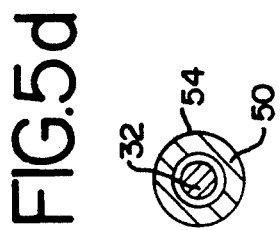
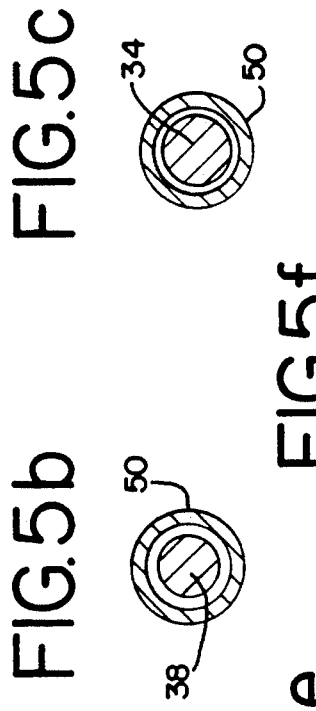
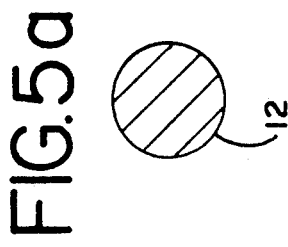

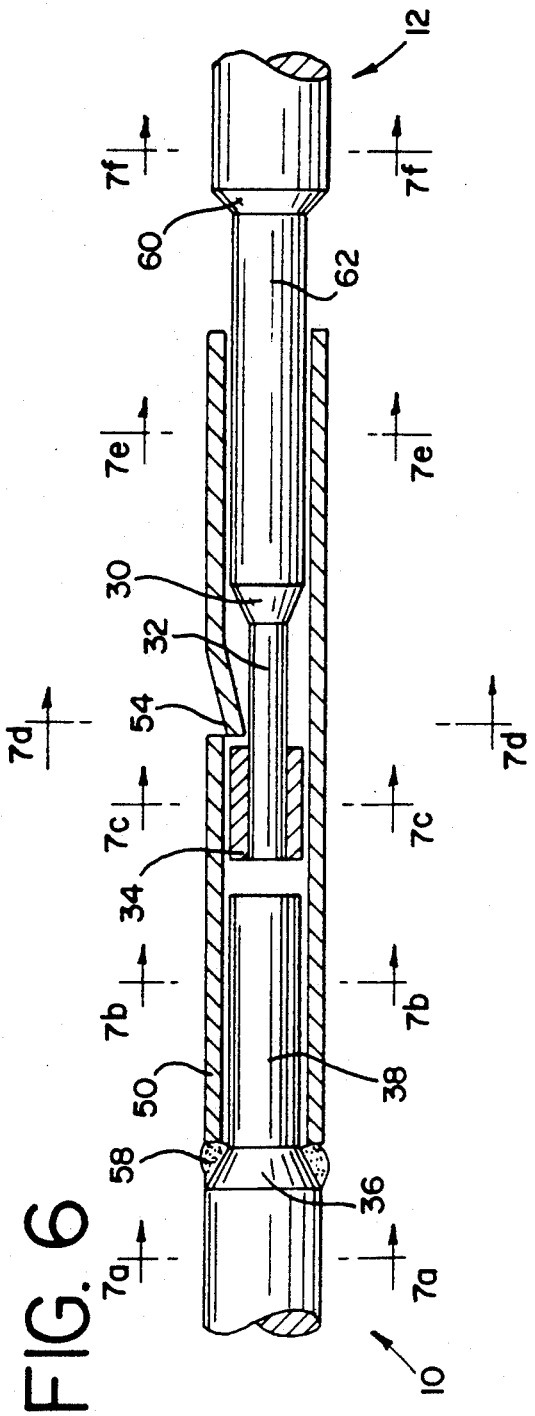

GUIDE WIRE WITH SWIVEL

BACKGROUND OF THE INVENTION

The present invention relates to intravascular guide wires and methods of use thereof. In particular, the present invention relates to an intravascular guide wire and methods of use to facilitate catheter exchange thereover.

One common use for guide wires is in coronary angioplasty which is a treatment for obstructive coronary artery disease. Obstructive coronary artery disease continues to be a serious health problem facing our society today. This disease is the result of the deposit of fatty substances on the interior of the walls of the arteries. The build-up, or lesion, of such deposits results in a narrowing of the inside diameter of the artery which in turn restricts the blood flow through the artery. This condition, wherein the opening of the artery is narrowed, is known as stenosis. Coronary artery bypass graft surgery may be used to treat this disease. Bypass surgery, however, may be extremely invasive and traumatic to the patent. Angioplasty is a less invasive and traumatic treatment for obstructive coronary artery disease.

Angioplasty is a procedure in which a balloon is positioned on the inside of the artery at the site of the lesion and expanded. In this procedure, an expandable balloon is attached to the distal end of a small diameter catheter which includes means for inflating the balloon from the proximal end of the catheter. The catheter is maneuvered or steered through the patent's vessels to the site of the lesion with the balloon in an uninflated form. When the uninflated balloon is properly positioned at the lesion, the balloon is then inflated to dilate the restricted area. The expansion of the balloon thus opens the restricted area of the artery.

One of the tasks associated with the positioning of the catheter is steering it through the blood vessels until it reaches the desired location. In order to accomplish this task, a guide wire may be used that is typically thinner than the catheter and easier to maneuver. Once the guide wire is inserted in the desired blood vessel and positioned across the stenosis, the catheter is slid over the guide wire, e.g. coaxially. The opening of the catheter that the guide fits coaxially within is commonly called a lumen.

Guide wires employed in coronary angioplasty are usually of relatively small diameter due to the combination of the small size of the relevant blood vessels and the even smaller size of the luminal openings of the dilatation catheter. Guide wires of a very small diameter, for example 0.010 to 0.018 inches, may be suitable for use in the narrow coronary vessels. Such guide wires may have an extremely floppy distal tip which may be bent or preformed by the physician to facilitate placement of the guide wire at the desired location.

Typically, a guide wire is longer than the catheter with which it is used for at least two reasons. First, at least a portion of the distal end of the guide wire extends past and through the distal end of the catheter. This distal end of the guide wire is usually much narrower and more flexible than the catheter, and may be biased in a preselected direction. This assists the physician in steering the catheter through the patient's vasculature. Second, the proximal end of the guide wire extends outwardly from the proximal portion of the catheter. During a procedure, both the proximal ends of the guide wire and the catheter remain outside the patient's body. The physician can steer the guide wire by torsionally rotating the proximal end of the guide wire. A portion of the proximal portion of the guide wire may also be advanced into or extracted from the catheter to either increase or decrease the amount of the guide wire extending from the distal portion of the catheter. Again, this extra length extending from the distal end of the catheter may allow the physician to better steer the guide wire or place it through narrower regions of the patient's vasculature. In coronary angioplasty, the catheter may be 135 centimeters long while the guide wire may be 175 centimeters long.

A problem associated with the use of guide wires, especially in the coronary vasculature, relates to exchanging catheters after the guide wire and catheter have already been inserted into the patient's body. An exchange may be required when, after the physician has placed one catheter into the patient, the physician determines that a different size catheter is needed. For example in coronary angioplasty, after steering the catheter substantially to the stenosis, the physician may find that the balloon selected is too large or too small. An exchange may also be needed to replace a balloon dilatation catheter with a different intravascular device, such as an atherectomy cutter, a stent, a diagnostic ultrasound catheter, etc. This may occur even after the guide wire is within the stenosed area. When an exchange is made, it is highly desirable that the guide wire remain in place. This prevents the physician from having to withdraw the guide wire, "re-steer" it through the patient's vasculature and cross the lesion again.

One way to affect a change without losing the positioning of the guide wire is for the physician to remove the existing guide wire while leaving the catheter in place and then replacing the existing guide wire with an exchange wire. The exchange wire is typically much longer than the original guide wire. For example, it may be 300 centimeters long. Once the exchange wire is in place, the physician removes the catheter from the patient over the exchange wire. While removing the catheter, the physician holds the proximal end of the exchange wire in place so that the distal end of the wire remains in the same position inside the patient's body. Without the longer exchange wire, the physician would have no way of holding the guide wire when removing the catheter, because the proximal end of the normal length guide wire would soon disappear into the catheter as the catheter was being extracted from the patient's body.

One disadvantage to this prior art method is that it takes time to change guide wires. Furthermore, the physician must again insert the distal-most tip of the exchange wire into the exact position desired. This is necessary because, as stated above, the distal end of the guide wire typically extends from the distal end of the catheter to "guide" the catheter. Each time the physician must reinsert the guide wire, there may be a risk of injury to the patient's vasculature. Also, this process of reinserting the distal end of the guide wire may be time consuming.

Although one solution to this problem might be to use a longer (for example double-length) guide wire in the first place, this also may pose a problem for the physician. For instance, the excess wire extending from the proximal end of the catheter may make it difficult to torsionally rotate the wire and steer it through the patient's vasculature.

U.S. Pat. No. 4,919,103 (Gambale et al.) attempts to solve these problems by providing a guide wire extension that is crimped onto a regular guide wire when needed. One disadvantage of this prior art is that, once crimped on, the extension is permanently attached to the guide wire. This permanent attachment causes similar disadvantages with maneuvering as expressed above with respect to the longer, one piece exchange wire.

Certain detachable and extendable guide wires have also been available. A disadvantage of some of these guide wire extension designs is that it can be time-consuming and tedious to connect an extension wire and then disconnect it after use.

Therefore, there is a need to provide a guide wire that provides adequate length for the purpose of exchanging catheters, while at the same time allowing the physician to steer the portion of the guide wire that is within the patient's body easily by torsional rotation from a proximal location.

Also, there is a need for a guide wire that has qualities that are desirable among guide wires generally, and that is also able to make the exchange of catheters easier. It is also desired that a longer guide wire that is still easy to steer be provided.

SUMMARY OF THE INVENTION

The invention relates to an intravascular guide wire made of a main part, an extension part, and a connector. The main part and the extension part are connected by the connector in a manner that allows the main part and the extension part to be rotated relative to each other.

The invention also relates to methods of use of the intravascular guide wire. In one embodiment of the invention, the main part and the extension part are provided separately and then permanently connected when the extension part is needed. In another embodiment, the extension part is held in a coiled orientation through the use of a coiled carrier tube.

BRIEF DESCRIPTION OF THE DRAWINGS

FIG. 1 shows an embodiment of the present invention.

FIG. 2 shows a portion of the embodiment of FIG. 1.

FIG. 3a shows a cross section of the embodiment of FIG. 2 along line 3a—3a.

FIG. 3b shows a cross section of the embodiment of FIG. 2 along line 3b—3b.

FIG. 3c shows a cross section of the embodiment of FIG. 2 along line 3c—3c.

FIG. 3d shows a cross section of the embodiment of FIG. 2 along line 3d—3d.

FIG. 3e shows a cross section of the embodiment of FIG. 2 along line 3e—3e.

FIG. 4 shows another embodiment of the present invention.

FIG. 5a shows a cross section of the embodiment of FIG. 4 along line 5a—5a.

FIG. 5b shows a cross section of the embodiment of FIG. 4 along line 5b—5b.

FIG. 5c shows a cross section of the embodiment of FIG. 3 along line 5c—5c.

FIG. 5d shows a cross section of the embodiment of FIG. 3 along line 5d—5d.

FIG. 5e shows a cross section of the embodiment of FIG. 4 along line 5e—5e.

FIG. 5f shows a cross section of the embodiment of FIG. 4 along line 5f—5f.

FIG. 6 shows yet another embodiment of the present invention.

FIG. 7a shows a cross section of the embodiment of FIG. 6 along line 7a—7a.

FIG. 7b shows a cross section of the embodiment of FIG. 6 along line 7b—7b.

FIG. 7c shows a cross section of the embodiment of FIG. 6 along line 7c—7c.

FIG. 7d shows a cross section of the embodiment of FIG. 6 along line 7d—7d.

FIG. 7e shows a cross section of the embodiment of FIG. 6 along line 7e—7e.

FIG. 7f shows a cross section of the embodiment of FIG. 6 along line 7f—7f.

DETAILED DESCRIPTION OF THE PRESENTLY PREFERRED EMBODIMENTS

Referring to FIG. 1 there is depicted a preferred embodiment of the present invention. This embodiment is a two-part intravascular guide wire with a swivel. The first part is a main part 10 and the second part is an extension part 12. The two parts 10, 12 are connected by a swivel 14. This swivel 14 is depicted in FIG. 2 in more detail. FIGS. 3a—3e are various cross sections of FIG. 2 as indicated. FIGS. 1, 2, and 3a—3e will be referred to together.

The main part 10 of guide wire is approximately 175 centimeters in length. The main part 10 has an outside diameter of approximately 0.014 inches except that the most distal 12 inches 15 of the main part 10 may be tapered in steps as is known in the art. The extension part 12 is approximately 125 centimeters long and substantially 0.014 inches in diameter throughout. The extension part 12 may be fairly flexible.

The extension part 12 may be held in a carrier tube 16 as is depicted in FIG. 1. The carrier tube 16 is made of any suitable material, for example polyethylene or a combination of 50% polyolefin and 50% high density polyethylene, and is held into a coiled orientation as shown in FIG. 1 by cavity clips 18 or any other suitable means. The carrier tube may be 0.10 inches in inside diameter, 0.14 inches in outside diameter, and approximately 300 centimeters in length.

Initially, the main part 10, the swivel 14, and the extension part 12 are held within the carrier tube 16 (for shipping, etc.). When using this device, the physician may slide the main part 10 and the swivel 14 out of the carrier tube 16 and leave all but a small portion of the extension part 12 in the carrier tube 16. This situation is depicted in FIG. 1. The benefits of this orientation will be discussed in detail below.

The guide wire, including most portions discussed herein, may be made of stainless steel. In a preferred embodiment, type 304 stainless steel may be used. Other appropriate materials are also within the scope of the invention. Unless otherwise noted, the material used for all elements of all embodiments disclosed below is stainless steel. Some portions of the guide wire may be made of other material to aid in the tracking of the guide wire through the patient's body.

At the distal end of the main part 10 is a floppy tip 24. The tip may be formed by methods known in the art and may include a helically coiled spring. This spring may be positioned coaxially over at least a portion of the tapered distal portion 15. The tip may be made of platinum or other material to facilitate viewing it on a fluoroscope and thus tracking the guide wire through the patient's body.

Portions of the guide wire may also include a polymer jacket (not shown) placed coaxially about it, or a polymer coating (not shown). The polymer jacket or coating may also cover the whole guide wire.

The description of the main part 10 and the extension part 12 is identical for all of the embodiments disclosed herein. In this respect, the embodiments of FIGS. 1,2,4,6, and the cross-sections thereof, are identical. The difference in these three preferred embodiments is how the swivel 14 is accomplished. Therefore, discussed below, are the three swivels for the three embodiments disclosed. For clarity, like elements of each embodiment are numbered consistently.

Referring now to FIGS. 2, 3a, 3b, 3c, 3d, and 3e, the swivel 14, which rotatably connects the main part 10 and the extension part 12, will now be described in detail. This embodiment can be called "pinched end swivel with weld ball."

Near the distal end of the extension part 12 is a taper 30. The taper 30 is approximately 1 inch long. This taper 30 is formed by centerless grinding.

Distal to the taper 30 is a narrow portion 32 of the extension part 12. This narrow portion 32 is approximately 0.45 inches long and 0.005 inches in diameter. At the most distal end of the narrow portion 32 is a weld ball 34. This weld ball 34 is substantially spherical and has a diameter of 0.009 inches. It may be formed by tig welding.

Near the proximal end of the main part 10, there is another taper 36. This taper 36 is 1 inch long and is formed by centerless grind. Proximal to the taper 36 is a narrow portion 38 of the main part 10. This narrow portion 38 is approximately 0.3 inches long and 0.009 inches in diameter.

Placed coaxially about the narrow portion 38, of the main part 10, the weld ball 34, and a portion of the narrow portion 32 of the extension part 12 is a sleeve 50. This sleeve 50, for its main portion, is substantially cylindrical. In all of the embodiments disclosed herein the sleeve 50 may be made out of hypotube. Besides the main portion, the sleeve 50 has a pinched end 54. The main portion of the sleeve 50 has an outside diameter of approximately 0.014 inches and an inside diameter of approximately 0.010 inches. The pinched end 54 has an inside diameter of approximately 0.006 inches. The total length of the sleeve 50, including the pinched end 54, is approximately 0.45 inches.

As can be seen in FIGS. 2, and 3a-3e, the most distal end of the sleeve 50 is placed coaxially about the narrow portion 38 of the main part 10. The sleeve is bonded 58 to the main part 10 in an area near the taper 36. This bonding is accomplished by silver soldering, although other bonding methods, such as brazing, adhesives, mechanical fit, etc., may also be acceptable. The weld ball 34 is also coaxially within the sleeve 50 as is a small portion of the narrow portion 32 of the extension part 12. Furthermore, a portion of the narrow portion 32 of the extension part 12 is coaxially within the pinched end 54. Because the diameter of the weld ball 34 is larger than the inside diameter of the pinched end 54, the weld ball 34 is held within the sleeve 50.

Therefore, as can be seen, the swivel 14 is constructed in such a way as to allow the main part 10 to be torsionally rotated independently of the extension part 12. This is possible because the diameter of the weld ball 34 is less than the inside diameter of the sleeve 50, and the diameter of the narrow portion 32 of the extension part 12 is less than the inside diameter of the pinched end 54. (See FIGS. 3c and 3d). It should be noted that the swivel is preferably not detachable.

Referring now to FIGS. 4, 5a, 5b, 5c, 5d, 5e, and 5f, there is shown a second preferred embodiment of the present invention. In this embodiment, the swivel 14 which rotatably connects the main part 10 and the extension part 12 will now be described in detail. This embodiment can be called "mid-waist swivel with weld ball."

Near the distal end of the extension part 12 is a first taper 60. The first taper 60 is approximately 1 inch long. This taper 60 is formed by centerless grinding. Distal to the taper 60 is a first narrow portion 62 of the extension part 12. This narrow portion 62 is approximately 0.6 inches long and 0.009 inches in diameter.

Distal to the first narrow portion 62 is a second taper 30. The second taper 30 is approximately 0.3 inches long. This taper 30 is formed by centerless grinding. Distal to the taper 30 is a second narrow portion 32 of the extension part 12. This narrow portion 32 is approximately 0.4 inches long and 0.005 inches in diameter. At the most distal end of the second narrow portion 32 is a weld ball 34. This weld ball is substantially spherical and has a diameter of 0.009 inches. It may be formed by tig welding.

Near the proximal end of the main part 10, there is a taper 36. This taper is 1 inch long and is formed by centerless grinding. Proximal to the taper 36 is a narrow portion 38 of the main part 10. This narrow portion 38 is approximately 0.3 inches long and 0.009 inches in diameter.

Placed coaxially about the narrow portion 38 of the main part 10, the weld ball 34, the second narrow portion 32, and a portion of the first narrow portion 62 of the extension part 12 is a sleeve 50. This sleeve is substantially cylindrical except for a pinched region 54. Besides the pinched region 54, the sleeve 50 has an outside diameter of approximately 0.014 inches and an inside diameter of approximately 0.01 inches. The pinched region 54 has an inside diameter of approximately 0.006 inches. The total length of the sleeve 50, including the pinched region 54, is approximately 1.25 inches. The distance from the most distal end of the sleeve 50 to the middle of the pinched region 54 is approximately 0.40 inches.

As can be seen in FIGS. 4 and 5a-5f, the most distal end of the sleeve 50 is placed coaxially about the narrow portion 38 of the main part 10. The sleeve is bonded 58 to the main part 10 in an area near the taper 36. This bonding is accomplished by silver soldering although other bonding methods, such as brazing, adhesives, mechanical fit, etc., may also be acceptable. The weld ball 34 is also coaxially within the sleeve 50 as is the second narrow portion 32 and a portion of the first narrow portion 62 of the extension part 12. Furthermore, a portion of the second narrow portion 32 of the extension part 12 is coaxially within the pinched region 54. Because the diameter of the weld ball 34 is larger than the inside diameter of the pinched region 54, the weld ball 34 is held within the sleeve 50.

Therefore, as can be seen, the swivel 14 is constructed in such a way as to allow the main part 10 to be torsionally rotated independently of the extension part 12. This is possible because the diameters of the weld ball 34 and the first narrow portion 62 are less than the inside diameter of the sleeve 50, and the diameter of the second narrow portion 32 of the extension part 12 is less than the inside diameter of the pinched region 54. (See FIGS. 5c, 5d, and 5e.) It should be noted that the swivel is preferably not detachable.

Referring now to FIGS. 6, 7a, 7b, 7c, 7d, 7e, and 7f, there is shown a third preferred embodiment of the present invention. In this embodiment, the swivel 14 which rotatably connects the main part 10 and the extension part 12 will now be described in detail. This embodiment can be called "mid snap swivel with slide-stop."

At the distal end of the extension part 12 is a first taper 60. The first taper 60 is approximately 1 inch long. This taper 60 is formed by centerless grinding. Distal to the taper 60 is a first narrow portion 62 of the extension part 12. This narrow portion 62 is approximately 0.4 inches long and 0.009 inches is diameter.

Distal to the first narrow portion 62 is a second taper 30. The second taper 30 is approximately 0.3 inches long. This taper 30 is formed by centerless grinding. Distal to the taper 30 is a second narrow portion 32 of the main part 10. This narrow portion 32 is approximately 0.3 inches long and 0.005 inches in diameter. At the most distal end of the second narrow portion 32 of the extension part 12 is a slide stop 34. This slide stop 34 is substantially cylindrical and has a diameter of approximately 0.009 inches and a length of approximately 0.14 inches. It is formed by sliding a small segment of hypotube over the second narrow portion 32 and bonding the hypotube to the second narrow portion 32. The bonding may be accomplished, for example, by silver soldering.

At the proximal end of the main part 10, there is a taper 36. This taper is 1 inch long and is formed by centerless grinding. Proximal to the taper 36 is a narrow portion 38 of the main part 10. This narrow portion 38 is approximately 0.3 inches long and 0.009 inches in diameter.

Placed coaxially about the narrow portion 38, of the main part 10, the slide stop 34, the second narrow portion 32, of the extension part 12 and a portion of the first narrow portion 62 of the extension part 12, is a sleeve 50. This sleeve 50 is substantially cylindrical except for a resilient snap 54. This snap is formed by making a small transverse cut in the sleeve 50, approximately one third of the way down through the cross section of the sleeve 50. Pressure is then put on one side of the cut in the sleeve 50 to deform it and form the resilient snap 54. The resilient snap 54 acts as a resilient arm and has a rest position (shown in FIGS. 6 and 7d) and an extended position (not shown) which will be described below. Besides the resilient snap 54, the sleeve 50 has an outside diameter of approximately 0.014 inches and an inside diameter of approximately 0.01 inches. The resilient snap 54 has an inside clearance when in the rest position of approximately 0.008 inches. The total length of the sleeve 50, including the resilient snap 54, is approximately 1.25 inches. The distance from the most distal end of the sleeve 50 to the beginning of the resilient snap 54 is approximately 0.50 inches.

As can be seen in FIGS. 6 and 7a-7f, the most distal end of the sleeve 50 is placed coaxially about the narrow portion 38 of the main part 10. The sleeve is bonded 58 to the main part 10 in an area near the taper 36. This bonding is accomplished by silver soldering, although other bonding methods, such as brazing, adhesives, mechanical fit, etc., may also be acceptable. The slide stop 34 is also coaxially within the sleeve 50 as is the second narrow portion 32 and a portion of the first narrow portion 62 of the extension part 12. Furthermore, a portion of the second narrow portion 32 of the extension part 12 is coaxially within the resilient snap 54. Because the diameter of the slide stop 34 is larger than the inside clearance of the resilient snap 54, the slide stop 34 is held within the sleeve 50.

Therefore, as can be seen, the swivel 14 is constructed in such a way as to allow the main part 10 to be torsionally rotated independently of the extension part 12. This is possible because the diameters of the slide stop 34 and the first narrow portion 62 are less than the inside diameter of the sleeve 50, and the diameter of the second narrow portion 32 of the extension part 12 is less than the inside diameter of the resilient snap 54. (See FIGS. 7c, 7d, and 7e.)

Although this swivel 14 is not detachable once engaged, it may be provided initially in a detached form. That is, the main part 10 and extension part 12 may be provided separately. If the user feels an extension is needed, the slide stop 34 and the narrow portions 32 and 62 of the extension part 12 may be inserted into the sleeve 50 (which is attached to the main part 10) until the slide stop 34 is slid past the resilient snap 54 As stated above, once advanced past the resilient snap 54, the slide stop 34 cannot be withdrawn. As the slide stop 34 is within the resilient snap 54, the resilient snap is in its expanded or stretched position. Once the slide stop 34 is advanced past the resilient snap 54, the resilient snap goes back into its rest or normal position and prevents the slide stop 34 from being withdrawn from the sleeve 50. It should be understood that after permanent engagement, the main part 10 can be torsionally rotated independently of the extension part 12.

With all of the embodiments, it will be understood by those skilled in the art that many other materials may be used. Also, one skilled in the art can recognize that the swivels may be reversed and that the above orientations are merely exemplary.

Finally, although it has been stated that the above embodiments allow the main part 10 to be torsionally rotated independently of the extension part 12, it should be understood that the extension part 12 can be torsionally rotated independently of the main part 10. In other words, the main part 10 and the extension part 12 can either (or both) be torsionally rotated independently of each other.

As can be readily seen, the disclosed invention is advantageous over the prior art. The physician has the extension readily available and, in the case of the first two embodiments, previously attached. This obviates the need to open extension wires and connect them. Furthermore, as can be seen in FIG. 1, the extension part may be coiled up in the carrier tube 16 when not being utilized, thereby remaining out of the way. The disclosed device can be provided in a carrier tube 16. When the physician uses the device, the main part 10, the swivel 14, and a small portion of the extension part 12 is withdrawn from the carrier tube 16. The majority of the extension part 14 may be left in the carrier tube 16 so that it is neat, compact, and not in the physician's way. While the extension part 12 is coiled, the swivel allows the physician to torsionally rotate the main part 10 without having to rearrange or move the extension part 12. Although the carrier tube is illustrated with only the first swivel embodiment it may be used with any of the embodiments disclosed herein.

The present guide wire with a swivel provides the length of a prior art wires with extensions while at the same time allowing the physician to torsionally rotate the main part without having to rotate the extension part. Thus, the physician can swivel the main part independently of the extension part and steer the main part easily. This guide wire can be used in many vessels in the body and is not meant to be exclusively for angioplasty. Furthermore, although presently preferred embodiments are presented, by varying the length, diameter, materials and/or other attributes of the disclosed guide wire embodiments, other embodiments of the claimed guide wire can be achieved for different uses such as in other vessels of different sizes of the body. For example, although a 0.014 inch diameter guidewire has been described above, the diameter of the guide wire may also be 0.010 inches, 0.012 inches, 0.016 inches, 0.018 inches, 0.020 inches, or any other diameter suitable for use in the medical field. The above embodiments are exemplary only. It is intended that the foregoing detailed description be regarded as illustrative rather than limiting and that it is understood that the following claims including all equivalents are intended to define the scope of the invention.

What is claimed is:

1. A guide wire comprising:
   a main part;
   an extension part;
   a coupling member, the coupling member connecting, the main part and the extension part such that the main part and the extension part can be rotated relative to each other, and wherein the coupling member allows the extension part to be permanently connected to the main part after the main part and the extension part are provided in a manner such that they are not initially connected.

2. The guide wire in claim 1 wherein the coupling member comprises a swivel.

3. The guide wire in claim 1 wherein the coupling member comprises a sleeve connected with one of the main part and the extension part and a slide stop connected to the other of either the main and the extension part, wherein the slide stop fits within the sleeve in such a manner so as to allow the slide stop to rotate within the sleeve.

4. The guide wire in claim 3 wherein the sleeve further comprises a resilient snap operative to allow the slide stop to be inserted at least a predetermined distance into the sleeve, and preventing the slide stop from being removed from the sleeve once it has been inserted said predetermined distance.

5. A guide wire comprising:
   a main part;
   an extension part; and
   means for permanently coupling the extension part to the main part after the main part and the extension part are provided in a manner such that they are not initially connected and the main part and the extension part can be rotated relative to each other.

6. The guide wire in claim 5 wherein the means for permanently coupling comprises a sleeve connected with one of the main part and the extension part and a slide stop connected to the other of either the main and the extension part, wherein the slide stop fits within the sleeve in such a manner so as to allow the slide stop to rotate within the sleeve.

7. The guide wire in claim 6 wherein the sleeve further comprises a means for allowing the slide stop to be inserted at least a predetermined distance into the sleeve, and preventing the slide stop from being removed from the sleeve once it has been inserted said predetermined distance.

8. The guide wire in claim 5 wherein the means for permanently coupling comprises a swivel.

9. A method of making a guide wire comprising:
   providing a main part of the guide wire;
   providing an extension part of the guide wire; and
   connecting the main part and the extension part with a coupling member such that the main part and the extension part can be rotated relative to each other and the coupling member allows the extension part to be permanently connected to the main part after the main part and the extension part are provided in a manner such that they are not initially connected.

10. The method of making a guide wire in claim 9 wherein the coupling member comprises a swivel.

11. The method of making a guide wire in claim 9 wherein the coupling member comprises a sleeve connected with one of the main part and the extension part and a slide stop connected to the other of either the main and the extension part, wherein the slide stop fits within the sleeve in such a manner so as to allow the slide stop to rotate within the sleeve.

12. The method of making a guide wire in claim 11 wherein the sleeve further comprises a resilient snap operative to allow the slide stop to be inserted at least a predetermined distance into the sleeve, and preventing the slide stop from being removed from the sleeve once it has been inserted said predetermined distance.

13. A method of performing an intravascular procedure comprising the steps of:
   providing an intravascular catheter of the over the wire type;
   providing a guide wire in a length at least twice as long as the catheter, said guide wire comprising:
      a distal portion adapted to advance the catheter thereover, and
      a proximal portion connected to the distal portion such that said proximal portion and said distal portion can rotate relative to each other;
   advancing the distal portion of the guide wire intravascularly;
   advancing the catheter over the guide wire intravascularly by holding onto a proximal end of the distal portion of the guide wire, said proximal portion extending proximally out of a proximal end of the catheter, and steering the guide wire by rotating the distal portion of the guide wire relative to the proximal portion;
   exchanging the first catheter for a second catheter;
   withdrawing the first catheter over the distal and proximal portions of the guide wire while maintaining the position of the distal portion of the guide wire intravascularly;
   advancing the second catheter over the proximal and distal portions of the guide wire while maintaining the position of the distal portion of the guide wire intravascularly.

14. The method of claim 13 in which steering further comprises the step of:
   steering the distal portion of the guide wire while maintaining the proximal portion relatively stationary.

15. A method of performing an intravascular procedure comprising the steps of:

providing an intravascular catheter of the over the wire type;

providing a guide wire, said guide wire comprising:
- a distal portion adapted to advance the catheter thereover, and
- a proximal portion adapted to advance the catheter thereover, connecting the proximal portion to the distal portion so that said proximal portion and said distal portion can rotate relative to each other;

advancing the distal portion of the guide wire intravascularly by holding onto a proximal end of the distal portion of the guide wire, said proximal portion extending proximally out of a proximal end of the catheter, and steering the guide wire by rotating the distal portion of the guide wire relative to the proximal portion while maintaining the proximal portion relatively stationary;

advancing the catheter over the guide wire intravascularly;

exchanging the first catheter for a second catheter;

withdrawing the first catheter over the distal and proximal portions of the guide wire while maintaining the position of the distal portion of the guide wire intravascularly; and advancing the second catheter over the proximal and distal portions of the guide wire while maintaining the position of the distal portion of the guide wire intravascularly.

16. A method of using a guide wire comprising:
providing a main part of the guide wire;
providing an extension part of the guide wire; and
connecting the main part and the extension part with a coupling member such that the main part and the extension part can be rotated relative to each other and the coupling member allows the extension part to be permanently connected to the main part after the main part and the extension part are provided in a manner such that they are not initially connected.

17. The method of using a guide wire in claim 16 wherein the coupling member comprises a swivel.

18. The method of using a guide wire in claim 16 wherein the coupling member comprises a sleeve connected with one of the main part and the extension part and a slide stop connected to the other of either the main and the extension part, wherein the slide stop fits within the sleeve in such a manner so as to allow the slide stop to rotate within the sleeve.

19. The method of using a guide wire in claim 18 wherein the sleeve further comprises a resilient snap operative to allow the slide stop to be inserted at least a predetermined distance into the sleeve, and preventing the slide stop from being removed from the sleeve once it has been inserted said predetermined distance.

* * * * *

UNITED STATES PATENT AND TRADEMARK OFFICE
CERTIFICATE OF CORRECTION

PATENT NO. : 5,247,942
DATED : September 28, 1993
INVENTOR(S) : Richard R. Prather et al.

It is certified that error appears in the above-indentified patent and that said Letters Patent is hereby corrected as shown below:

On the title page, item (56):
IN THE REFERENCES CITED

On the title page under "U.S. PATENT DOCUMENTS" delete "4,992,923" and substitute therefor --4,922,923--.

In column 1, line 23, delete "patent" and substitute therefor --patient--.

In column 1, line 32, delete "patent's" and substitute therefor --patient's--.

In column 8, line 24, after "54" insert --.--.

UNITED STATES PATENT AND TRADEMARK OFFICE
CERTIFICATE OF CORRECTION

PATENT NO. : 5,247,942
DATED : September 28, 1993
INVENTOR(S) : Richard R. Prather, et. al.

It is certified that error appears in the above-indentified patent and that said Letters Patent is hereby corrected as shown below:

In column 9, line 2, before "prior" delete "a".

Signed and Sealed this

Twenty-sixth Day of April, 1994

Attest:

BRUCE LEHMAN

*Attesting Officer*       *Commissioner of Patents and Trademarks*